United States Patent [19]

Mikulicz

[11] 4,234,750
[45] Nov. 18, 1980

[54] HF ALKYLATION PROCESS
[75] Inventor: Michael Z. Mikulicz, Palatine, Ill.
[73] Assignee: UOP Inc., Des Plaines, Ill.
[21] Appl. No.: 69,683
[22] Filed: Aug. 27, 1979
[51] Int. Cl.³ .......................... C07C 2/18; C07C 2/60
[52] U.S. Cl. .................................. 585/332; 585/529; 585/719; 585/723
[58] Field of Search ................ 585/332, 529, 719, 723

[56] References Cited

U.S. PATENT DOCUMENTS

| | | | |
|---|---|---|---|
| 2,826,620 | 3/1958 | Matuszak | 585/332 |
| 3,309,421 | 3/1967 | Kirk et al. | 585/529 |
| 3,544,653 | 12/1970 | Webb et al. | 585/332 |
| 3,662,020 | 5/1972 | Hemminger et al. | 585/332 |
| 3,981,942 | 9/1976 | Zabransky | 585/701 |
| 4,139,573 | 2/1979 | Carson | 585/717 |

*Primary Examiner*—C. Davis
*Attorney, Agent, or Firm*—James R. Hoatson, Jr.; Robert W. Welch; William H. Page, II

[57] ABSTRACT

An improvement is disclosed in a process for the acid-catalyzed alkylation of an isoparaffin with an olefin alkylating agent. The improvement relates to an alkylation process wherein the hydrocarbon phase of the alkylation reaction mixture is introduced into a common fractionation column with a field butane stream comprising olefinic materials. The improvement comprises initially clay-treating said field butane stream.

12 Claims, 1 Drawing Figure

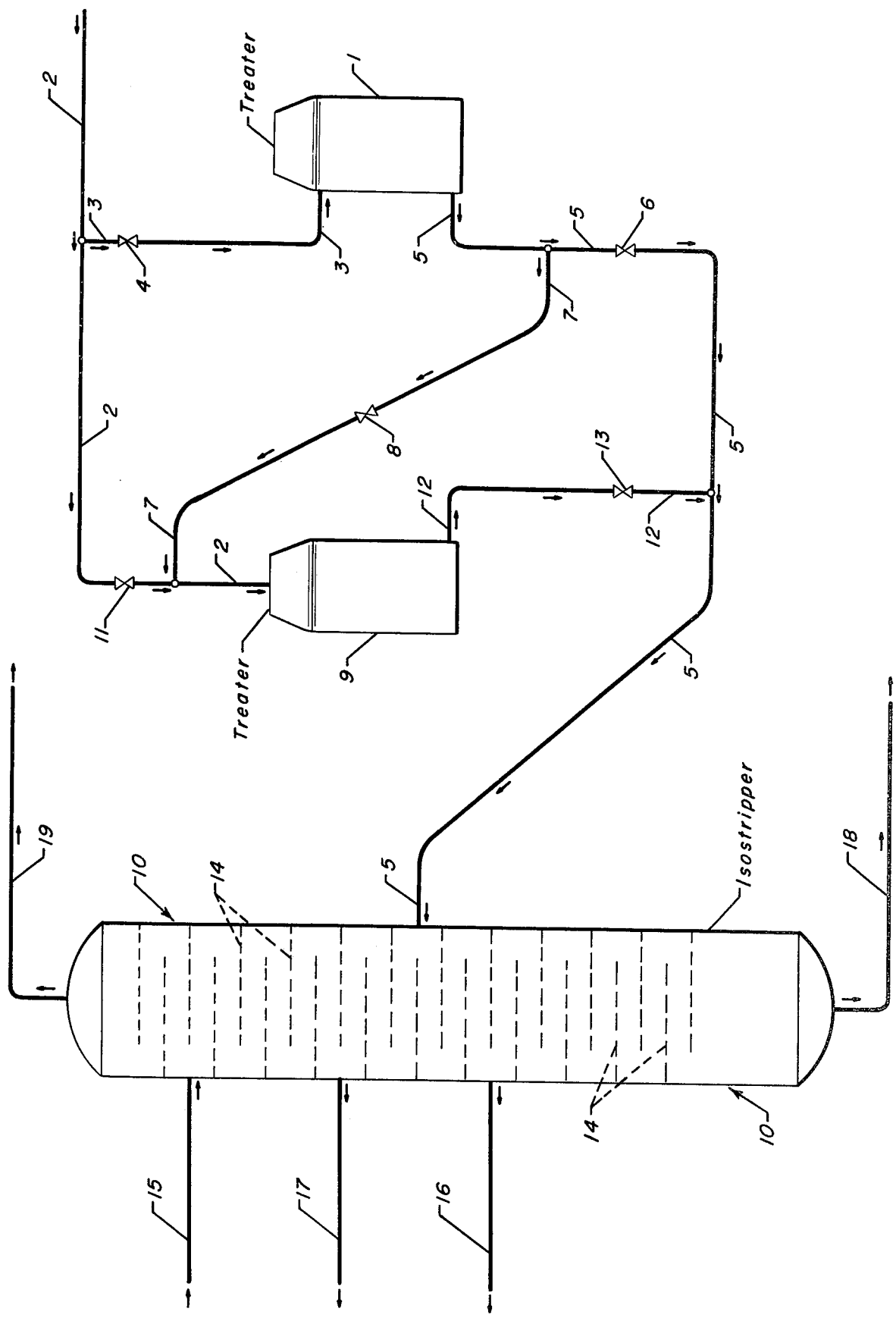

HF ALKYLATION PROCESS

This invention relates to the acid-catalyzed alkylation of an isoparaffin with an olefin alkylating agent. More particularly, this invention relates to the hydrofluoric acid-catalyzed alkylation of isobutane with a $C_3$-$C_4$ olefin alkylating agent to provide a motor fuel alkylate product.

In the acid-catalyzed alkylation process, a molar excess of the isoparaffin reactant is admixed with the olefin alkylating agent and treated in contact with the acid catalyst in an alkylation reactor at alkylation reaction conditions. The alkylation reaction mixture recovered from the alkylation reactor is allowed to settle into an acid phase and an acid-immiscible hydrocarbon phase comprising alkylate and unreacted isoparaffin. The hydrocarbon phase will almost invariably contain at least trace amounts of the acid catalyst. It is common practice to introduce the hydrocarbon phase into a fractionation column, frequently referred to as an isostripper, wherein the unreacted isoparaffin and acid catalyst are separated for recycle to the alkylation reactor, and the alkylate is separated and recovered as product.

Although applicable to the alkylation of a $C_4$-$C_7$ isoparaffin with a $C_3$-$C_7$ olefin alkylating agent, the present invention is particularly concerned with the alkylation of isobutane with a $C_3$-$C_4$ olefin alkylating agent. Field butanes, comprising a mixture of LPG products and by-products of other hydrocarbon conversion processes which constitute a typical refinery operation, are a principal source of the isobutane reactant. It has been a convenient practice to separate the isobutane from the field butanes in the same fractionation column wherein the aforesaid hydrocarbon phase is treated for the separation of unreacted isobutane. In this manner, fresh or make-up isobutane is recovered from the fractionation column in common with the recycle isobutane to furnish the total isobutane charge to the alkylation reactor.

It has been observed that certain LPG streams contain varying amounts of olefinic materials which tend to polymerize at conditions encountered in the separation process. With the accumulation of the polymeric materials, the trays embodied in the fractionation column or isostripper become progressively fouled with a resultant loss in column efficiency. Among other things, said fouling causes a loss of the acid catalyst present in the isostripper—the loss occurring as a result of the formation of organic fluorides which exit the isostripper with the product stream.

It is therefore an object of this invention to provide an improvement in a process for the acid-catalyzed alkylation of an isoparaffin with an olefin alkylating agent wherein the hydrocarbon phase of the alkylation reaction mixture and field paraffins are treated in a common fractionation column, said improvement substantially obviating polymer formation in said column, and the loss of acid catalyst therein.

Thus, in one of its broad aspects, the present invention relates to a process for the acid-catalyzed alkylation of an isoparaffin with an olefin alkylating agent wherein the hydrocarbon phase of the alkylation reaction mixture comprising alkylate, unreacted isoparaffin and at least trace amounts of acid, and field paraffins comprising isoparaffins, n-paraffins and olefins, are introduced into a common fractionation column wherein said alkylate, n-paraffins and isoparaffins are separated at conditions conducive to the polymerization of said olefins, and embodies the improvement which comprises initially treating said field paraffins in contact with a siliceous material effecting the separation of said olefins from said field paraffins; and thereafter introducing said field paraffins into said common fractionation column together with said hydrocarbon phase of said alkylation reaction mixture.

More specifically, this invention relates to a process for the hydrofluoric acid-catalyzed alkylation of isobutane with a $C_3$-$C_4$ olefin alkylating agent wherein the hydrocarbon phase of the alkylation reaction mixture comprises alkylate, unreacted isobutane and at least trace amounts of hydrofluoric acid, and field butanes comprising isobutane, n-butane and $C_3$-$C_4$ olefins, are introduced into a common fractionation column wherein said alkylate, n-butane and isobutane are separated at conditions conducive to the polymerization of said olefins, and embodies the improvement which comprises initially treating said field butanes at a temperature of from about 150° to about 200° F. in contact with attapulgus clay; and thereafter introducing said field butanes into said common fractionation column together with said hydrocarbon phase of said alkylation reaction mixture.

Other objects and embodiments of this invention will become apparent in the following detailed specification.

U.S. Pat. No. 3,981,942 is exemplary of an alkylation process such as herein contemplated. The cited patent illustrates a process wherein the hydrocarbon phase of an alkylation reaction mixture (line 18) containing at least a trace amount of hydrofluoric acid, and a field butane stream (line 20) are introduced into a common fractionation column or isostripper (19). Pursuant to the present invention, the field butane stream is first treated in contact with a siliceous material effecting the separation of olefinic materials. The selected siliceous material should be effective at a temperature of from about 80° to about 400° F., and preferably at a temperature of from about 150° to about 350° F., to catalyze the oligomerization and/or polymerization of the olefinic impurities contained in the field butanes. The siliceous materials herein contemplated are acidic in character somewhat in keeping with the siliceous materials associated with traditional clay-treating systems. Said materials include the naturally occurring clays and silicates, for example diatomaceous earth, fuller's earth, kieselguhr, attapulgus clay, feldspar, montmorillonite, halloysite, kaolin, bentonite, and the like, and especially those clays and silicates which have been activated by thermal and/or chemical treatment. The various clays and silicates are not necessarily equally effective under all treating conditions. However, of the naturally occurring clays and silicates, attapulgus clay and kieselguhr are preferred. Attapulgus clay, or kieselguhr which has been composited with phosphoric acid, are particularly effective. In one preferred embodiment of this invention, the field butanes are treated at a temperature of from about 150° to about 200° F. in contact with attapulgus clay. Synthetically prepared siliceous materials including silica, or silica in combination with alumina, zirconia, magnesia, etc., are also useful in the practice of this invention. The latter include the crystalline aluminosilicates or molecular sieves. It is also contemplated that certain of the proprietary clays and silicates, e.g., Filtrol 24, can be advantageously employed.

The further description of the improvement of this invention is presented with reference to the attached schematic drawing representing one preferred embodiment of the invention. Referring then to the drawing, a field butane stream is charged to a first clay treater 1 at a rate to provide about 500 moles of make-up isobutane per hour to an alkylation reactor, not shown. About 907 moles of n-butane, 10 moles of propane, 11 moles of propylene and 12 moles of butylenes are charged to the first clay treater 1 as other components of the field butane stream. The field butane stream is initially charged to the alkylation process through line 2 and is diverted through line 3 and an open block valve 4 to the first clay treater 1. The field butane stream is processed through the first clay treater in contact with particulate attapulgus clay. The field butane stream is so processed at a liquid hourly space velocity of about 4, a temperature of 150°–200° F., and a pressure to maintain substantially liquid phase treating conditions, it being desirable to treat the field butanes at about the bubble point of the liquid in contact with said clay particles. The field butane stream is withdrawn from the first clay treater 1 through line 5 and is transferred to a second clay treater 9, through an open block valve 8 contained in line 7, and by way of line 2. A block valve 11 is maintained in the closed position until such time that it becomes necessary or desirable to replace or regenerate the clay contained in the first clay treater 1. In that event, block valves 4, 6 and 8 will be closed off, and the field butane stream will be diverted through the open block valve 11 and continued through line 2 to the second clay treater 9. The treated field butane stream will then be withdrawn from said treater through an open block valve 13 contained in line 12, and said stream will be directed through line 5 to the isostripper 10.

In the normal pattern of flow, the field butane stream will be withdrawn from the first clay treater 1 through line 5 and transferred to the second clay treater 9 by way of line 7 as heretofore mentioned. The field butane stream is processed through the second clay treater 9 at substantially the same treating conditions employed in the first clay treater 1. The field butane stream is withdrawn from the second clay treater 9 through an open block valve 13 contained in line 12, and is transferred to the isostripper 10 through line 5 substantially free of olefinic materials. The isostripper 10 is a fractionation column containing the conventional reboiling means, refluxing means, and the like, and is shown comprising a multitude of perforated trays 14. The field butane stream, at a temperature of about 120°–140° F., enters the upper section of the isostripper 10 via line 5 at a rate to provide about 500 moles of make-up isobutane per hour. About 907 moles of n-butane and 10 moles of propane are introduced into the isostripper as components of the field butane stream. Any polymer formed from the treating operation will also be routed to the isostripper and will exit with the alkylate product. About 3,550 moles of unreacted isobutane, 600 moles of alkylate, 570 moles of n-butane, 325 moles of propane and 133 moles of hydrofluoric acid are also charged to the isostripper 10 per hour as the separated hydrocarbon phase of an alkylation reaction mixture, said hydrocarbon phase being charged to the isostripper through line 15 after being preheated to about 170° F. A sidecut, rich in n-butane, is recovered from the isostripper through line 16 at a rate of about 475 moles per hour and is subjected to treatment with potassium hydroxide for the removal of trace quantities of hydrofluoric acid. The isostripper 10 is operated at a bottom temperature of about 371° F. and at a pressure of about 160 psig. The top temperature is about 140° F. and the top pressure is about 152 psig. The normally liquid alkylate product is recovered through line 18 to provide about 600 moles per hour, and the alkylate product may be subjected to treatment with potassium hydroxide for acid removal. An isobutane-rich stream, including about 500 moles of n-butane, 225 moles of propane and 3,820 moles of isobutane per hour, is recycled via line 17 to an alkylation reactor, not shown. Also recovered and recycled through line 17 is about 60 moles of hydrofluoric acid per hour. Overhead vapors comprising about 110 moles of propane, 25 moles of n-butane, 230 moles of isobutane and about 70 moles of hydrofluoric acid per hour are withdrawn through line 19 for treatment in a propane and/or hydrofluoric acid stripper which is not shown.

I claim as my invention:

1. In a process for the acid-catalyzed alkylation of an isoparaffin with an olefin alkylating agent wherein the hydrocarbon phase of the alkylation reaction mixture comprising alkylate, unreacted isoparaffin and at least trace amounts of acid, and field paraffins comprising isoparaffins, n-paraffins and olefins, are introduced into a common fractionation column wherein said alkylate, n-paraffins and isoparaffins are separated at conditions conducive to olefin polymerization, the improvement which comprises:
    (a) initially treating said field paraffins in contact with a siliceous material effecting the separation of said olefins from said field paraffins; and,
    (b) thereafter introducing said field paraffins into said common fractionation column together with said hydrocarbon phase of said alkylation reaction mixture.

2. The improvement of claim 1 further characterized in that said acid-catalyzed alkylation process is a hydrofluoric acid-catalyzed alkylation process.

3. The improvement of claim 1 further characterized in that said isoparaffin is a $C_4$-$C_7$ isoparaffin.

4. The improvement of claim 1 further characterized in that said isoparaffin is isobutane, and said field paraffins comprise n-butane, isobutane and a $C_3$-$C_4$ olefin.

5. The improvement of claim 1 further characterized in that said olefin alkylating agent is a $C_3$-$C_7$ olefin.

6. The improvement of claim 1 further characterized in that said olefin alkylating agent is a $C_3$-$C_4$ olefin.

7. The improvement of claim 1 further characterized in that said field paraffins are treated in contact with said siliceous material at a temperature of from about 80° to about 400° F.

8. The improvement of claim 1 further characterized in that said field paraffins are treated in contact with said siliceous material at a temperature of from about 150° to about 350° F.

9. The improvement of claim 1 further characterized in that said siliceous material comprises kaolin.

10. The improvement of claim 1 further characterized in that said siliceous material comprises kieselguhr.

11. The improvement of claim 1 further characterized in that said siliceous material is a composite of kieselguhr and phosphoric acid.

12. The improvement of claim 1 further characterized in that said field paraffins are treated in contact with attapulgus clay at a temperature of from about 150° to about 200° F.

* * * * *